US009795521B2

(12) United States Patent
Fisher

(10) Patent No.: US 9,795,521 B2
(45) Date of Patent: Oct. 24, 2017

(54) EMERGENCY VEHICLE CONTROL APPLICATION

(71) Applicant: Horton Emergency Vehicles, Grove City, OH (US)

(72) Inventor: Eric Fisher, Columbus, OH (US)

(73) Assignee: Halcore Group, Inc., Grove City, OH (US)

( * ) Notice: Subject to any disclaimer, the term of this patent is extended or adjusted under 35 U.S.C. 154(b) by 0 days.

(21) Appl. No.: 14/158,901

(22) Filed: Jan. 20, 2014

(65) Prior Publication Data

US 2015/0088339 A1 Mar. 26, 2015

Related U.S. Application Data

(60) Provisional application No. 61/881,197, filed on Sep. 23, 2013.

(51) Int. Cl.
*B60R 25/01* (2013.01)
*A61G 3/00* (2006.01)
*G06F 19/00* (2011.01)

(52) U.S. Cl.
CPC ........... *A61G 3/00* (2013.01); *G06F 19/3418* (2013.01)

(58) Field of Classification Search
CPC ............ G06F 7/00; B60R 16/02; B60R 25/01
USPC ............................................................ 701/2
See application file for complete search history.

(56) References Cited

U.S. PATENT DOCUMENTS

| 6,188,939 | B1 * | 2/2001 | Morgan et al. ................. 701/36 |
| 6,411,874 | B2 * | 6/2002 | Morgan et al. ................. 701/36 |
| 6,960,990 | B2 * | 11/2005 | McKibbon ............... 340/426.35 |
| 7,356,474 | B2 * | 4/2008 | Kumhyr ........................ 704/275 |
| 7,366,892 | B2 * | 4/2008 | Spaur et al. .................. 713/151 |
| 7,406,423 | B2 * | 7/2008 | Kumhyr ........................ 704/275 |
| 7,522,980 | B2 * | 4/2009 | Watkins et al. .............. 701/29.5 |
| 8,433,763 | B2 * | 4/2013 | Anderson et al. ............ 709/206 |
| 2008/0027602 | A1 * | 1/2008 | Yeap ....................... B60R 25/04 701/31.4 |
| 2009/0239587 | A1 * | 9/2009 | Negron ............... G06F 3/04883 455/566 |
| 2009/0289757 | A1 * | 11/2009 | Ballard ......................... 340/3.1 |
| 2012/0028580 | A1 * | 2/2012 | Oesterling et al. .......... 455/41.2 |
| 2012/0116608 | A1 * | 5/2012 | Park et al. ........................ 701/2 |

* cited by examiner

*Primary Examiner* — Adam Tissot
*Assistant Examiner* — Michael Berns
(74) *Attorney, Agent, or Firm* — Hovey Williams LLP

(57) ABSTRACT

A system, method, and computer program for remotely controlling a plurality of functions of an emergency vehicle, wherein at least one of the functions is activating the emergency lights. The method comprises connecting a mobile computing device to a central control unit through a wireless network, inputting a command on the mobile computing device, transmitting the command to the central control unit through the network, and performing the one or more functions of the emergency vehicle. Also provided is a computer program and a system for enabling a plurality of mobile computing devices to connect to at least one emergency vehicle, wherein an administrator may, among other things, control user access levels and vehicle functionality.

21 Claims, 12 Drawing Sheets

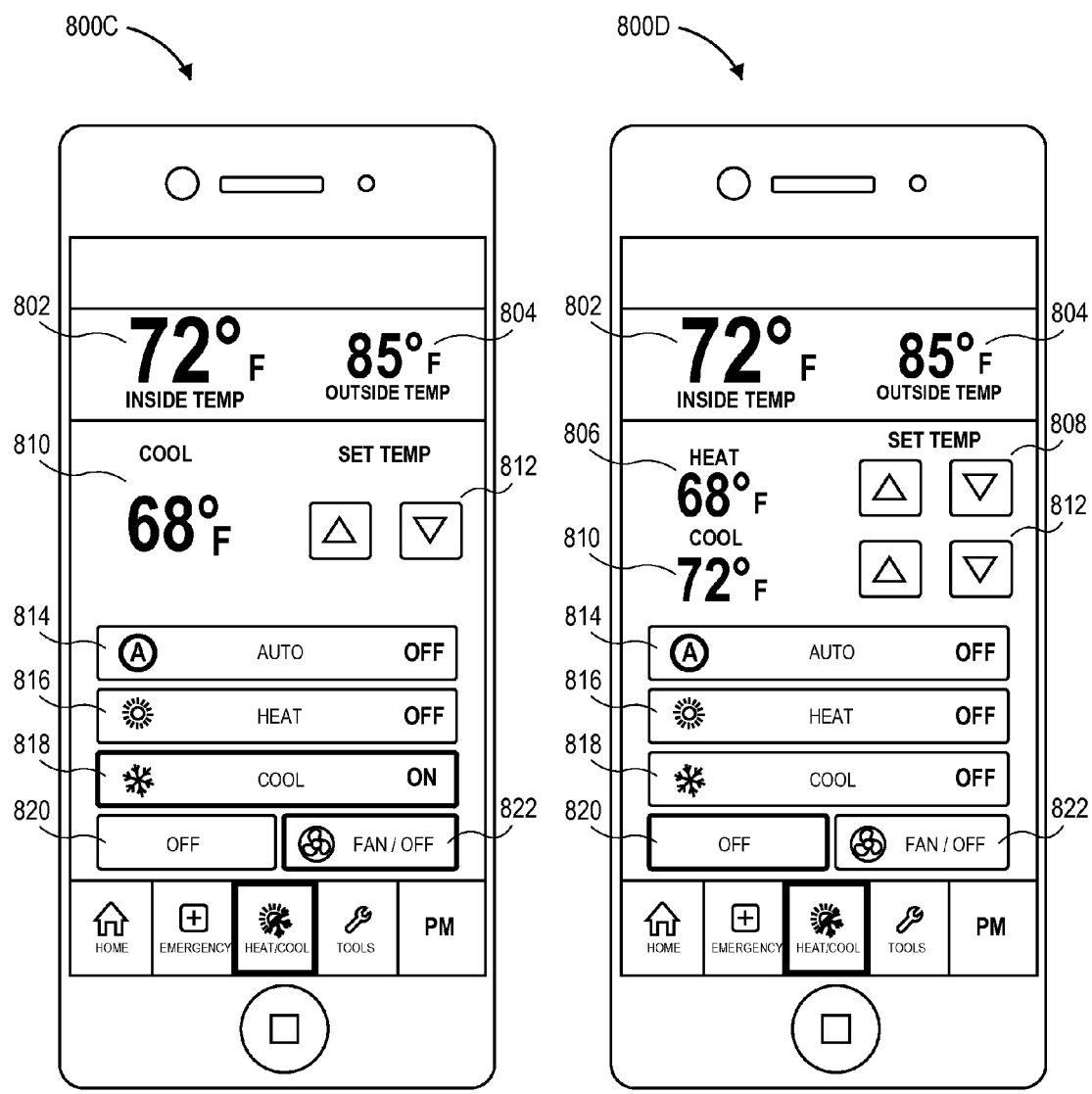

EMERGENCY VEHICLE CONTROL APPLICATION

CROSS-REFERENCE TO RELATED APPLICATIONS

The present application claims the priority benefit of U.S. Provisional Patent Application Ser. No. 61/881,197, filed Sep. 23, 2013, entitled "EMERGENCY VEHICLE CONTROL APPLICATION," incorporated by reference in its entirety herein.

BACKGROUND

1. Field of the Invention

Embodiments of the invention are directed to a system, method, and computer program for remotely controlling an emergency vehicle using a mobile computing device. More particularly, embodiments of the invention are directed to an emergency vehicle remote control system capable of controlling predetermined functions, wherein the remote operation is instructed by a mobile computing device via a network.

2. Description of the Related Art

Although remote control systems for remotely controlling vehicle functions are generally known, the remote control device is commonly embodied in a hand-held device that communicates through radio frequencies and is limited in functionality. Most remote control systems for vehicles are limited to remote keyless entry or remote keyless ignition. Remote keyless entry permits user access to automobiles by locking or unlocking doors without the physical use of a key in the locking mechanisms. Remote keyless ignition systems allow users to remotely start the engine of an automobile without the physical engagement of the key to the ignition system. Other limited vehicle functions remotely enabled by vehicle remote control systems may generally be available; however, product availability is limited, resulting in non-uniform standards of remote communication and the need for multiple remote controllers to perform the a plurality of functions. In the realm of emergency vehicles, the administration of an entire fleet would be necessary. Present day vehicle remote control systems are not configured to allow for administration and programmability of multiple remotes to multiple vehicles.

Emergency vehicle electrical systems have become more centralized, such that many of the functions of the emergency vehicle can be controlled by an onboard computer or control console. Although the control console is operable to control many of the functions of the emergency vehicle, the controls are typically limited to in-cabin access. Thus, if emergency personnel or an emergency vehicle operator were assisting with an emergency matter "on scene," they would have to remove themselves from the scene in order to prepare the vehicle manually. Whether related to cabin temperatures, activating emergency lights, warming the engine, or even running system diagnostics, all of the above activities would need to be performed within the cabin of the vehicle.

Accordingly, there is a need for a remote control system for remotely controlling a variety of functions of an emergency vehicle, without the inconvenience of multiple remotes. There is a greater need for the simplified administration of multiple users to multiple emergency vehicles, such that a remote device can be customized and reprogrammed with relative ease. Additionally, there is a need for a vehicle remote control system operable to provide an emergency vehicle operator with system diagnostics, maintenance reminders, real-time vehicle status, and active feedback.

SUMMARY

Embodiments of the invention solve the above-mentioned problems by providing a system, method, and computer program for remotely controlling an emergency vehicle using a mobile computing device. The emergency vehicle remote control system includes at least a central control unit and a communications module, both operably connected to the emergency vehicle, and a mobile computing device for remotely sending and receiving communications with the central control unit via the communications module.

The invention further provides for a mobile computing device having an executable program for controlling a variety of functions in an emergency vehicle. In one embodiment, the executable program uses available wireless network technology to communicate with the communications module of an emergency vehicle. The executable program is operable to display a plurality of functions to be performed on the emergency vehicle, receive an input from a user related to the function, and send a command that corresponds to the input to the central control unit of the emergency vehicle for performing the command.

In one embodiment of the invention, the emergency vehicle has a plurality of modules that are operably connected to the central control unit. The modules are operable to control or serve various functions of the vehicle, such as enable/disable emergency lights, remote start/kill, remote entry/lock, change thermostat settings, read vehicle diagnostics, and provide maintenance reminders. Other embodiments may be configured to incorporate specific module functionality for particular vehicular functions, into a specific module unit, or combine functionality and features of one or more modules.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWINGS

Embodiments of the invention are described in detail below with reference to the attached drawing figures, wherein:

FIG. 8C is a third screen capture of the computer program of embodiments of the present invention and illustrating a mobile computing device GUI and, in particular, an emergency vehicle Heat/Cool function control screen for setting the cool thermostat;

FIG. 8D is a fourth screen capture of the computer program of embodiments of the present invention and illustrating a mobile computing device GUI and, in particular, an emergency vehicle Heat/Cool function control screen for turning off vehicle climate control;

Figure 1:
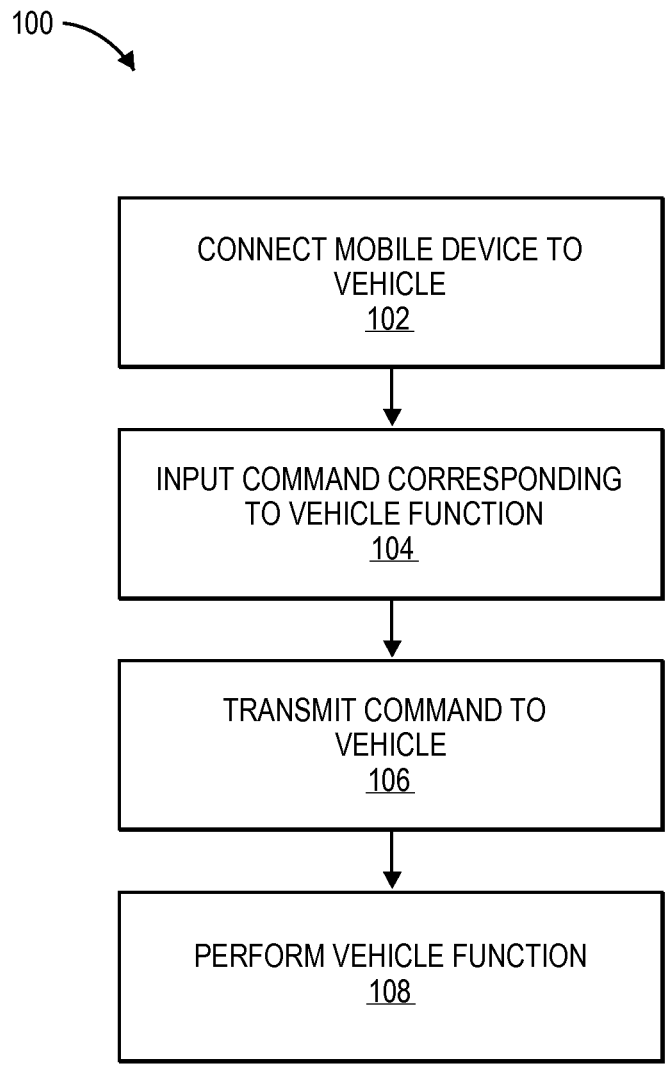
FIG. 1 is a flow chart of a method of remotely controlling an emergency vehicle.
Figure 2:
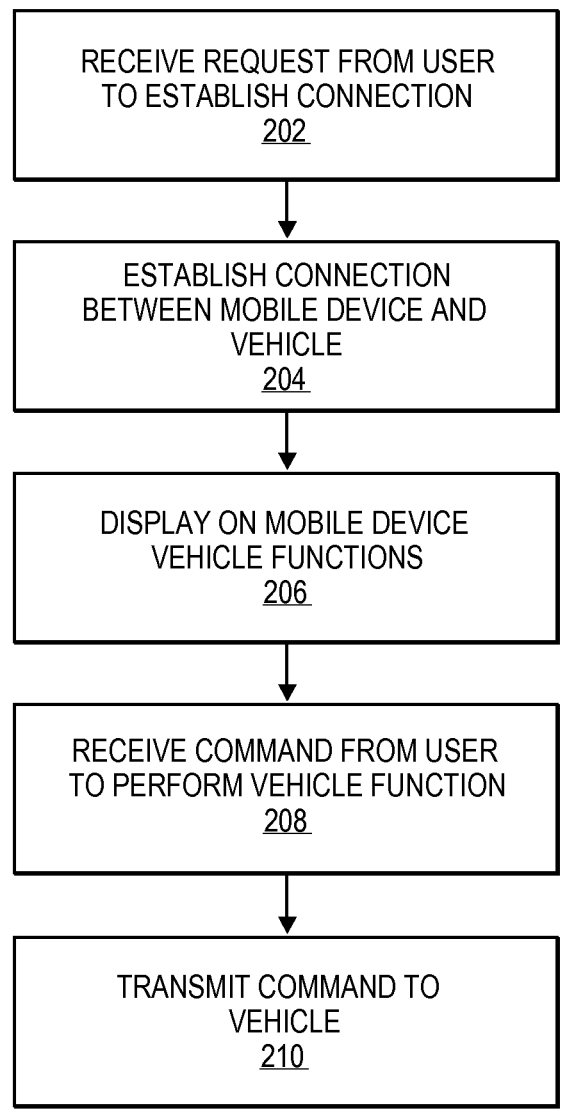
FIG. 2 is a flow chart of a computer program used to perform the method of remotely controlling an emergency vehicle.

The drawing figures do not limit the invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Embodiments of the invention are directed to a system, method, and computer program for remotely controlling an emergency vehicle using a mobile computing device. As referred to herein, the term "emergency vehicle" broadly relates to vehicles used by emergency response personnel, such as ambulances, fire trucks, patrol cars, and any other vehicle that may comprise a siren and/or emergency lights. The term "central control unit" refers to the onboard vehicle computer that is operably connected to the electrical system of the emergency vehicle and configured to perform various functions on components also operably connected to the electrical system of a vehicle. The central control unit is generally a computing device as further defined herein.

The computer program of embodiments of the invention comprises a plurality of code segments executable by a computing device for performing the steps of the method of the invention. The steps of the method may be performed in the order shown in FIG. 1, or they may be performed in a different order, unless otherwise expressly stated. Furthermore, some steps may be performed concurrently as opposed to sequentially. Also, some steps may be optional or substituted.

The user of the invention may choose various screens on the mobile computing device for selectively viewing operational features. The computer program of the invention may include a single view or a plurality of views, each view having a variety of available functions to control by the user. Functions available for view and control may be customized by the user, or may be controlled by an administrator. The arrangement of views and functions available on the computer program of the invention are not necessarily fixed, such that various view arrangements and layouts are plausible. Embodiments may comprise a plurality of virtual on/off switches, input keypads, and/or adjustment sliders for allowing the user to control various functions of the emergency vehicle. Embodiments may also allow for shortcut keys configured to perform a plurality of functions in sequence, in a predefined order, simultaneously, or at particular time intervals.

The method of embodiments of the invention may broadly comprise the steps 100 of connecting a mobile computing device to a central control unit through a wireless network 102, inputting a command on the mobile computing device 104, transmitting the command to the central control unit through the network 106, and performing the one or more functions of the emergency vehicle 108. The computer program of embodiments of the invention may broadly comprise the steps 200 of receiving, on a mobile computing device, a request from a user to establish a connection to the central control unit 202; establishing a wireless connection between the mobile computing device and the central control unit 204; displaying, on the mobile computing device, a plurality of functions of the emergency vehicle 206, wherein at least one function is activate emergency lights; receiving, on the mobile computing device, a command from the user to perform one or more functions of the emergency vehicle 208; and transmitting, from the mobile computing device, the command to the central control unit 210.

The system of embodiments of the invention may broadly comprise computing devices, servers, and communications networks to facilitate the functions and features described herein. The computing devices and servers may comprise any number and combination of processors, controllers, integrated circuits, programmable logic devices, or other data and signal processing devices for carrying out the functions described herein, and may additionally comprise one or more memory storage devices, transmitters, receivers, and/or communication busses for communicating with the various devices of the system. In various embodiments of the invention, the computing devices may comprise a memory element, a communication component, a display, and/or a user interface.

Figure 3:
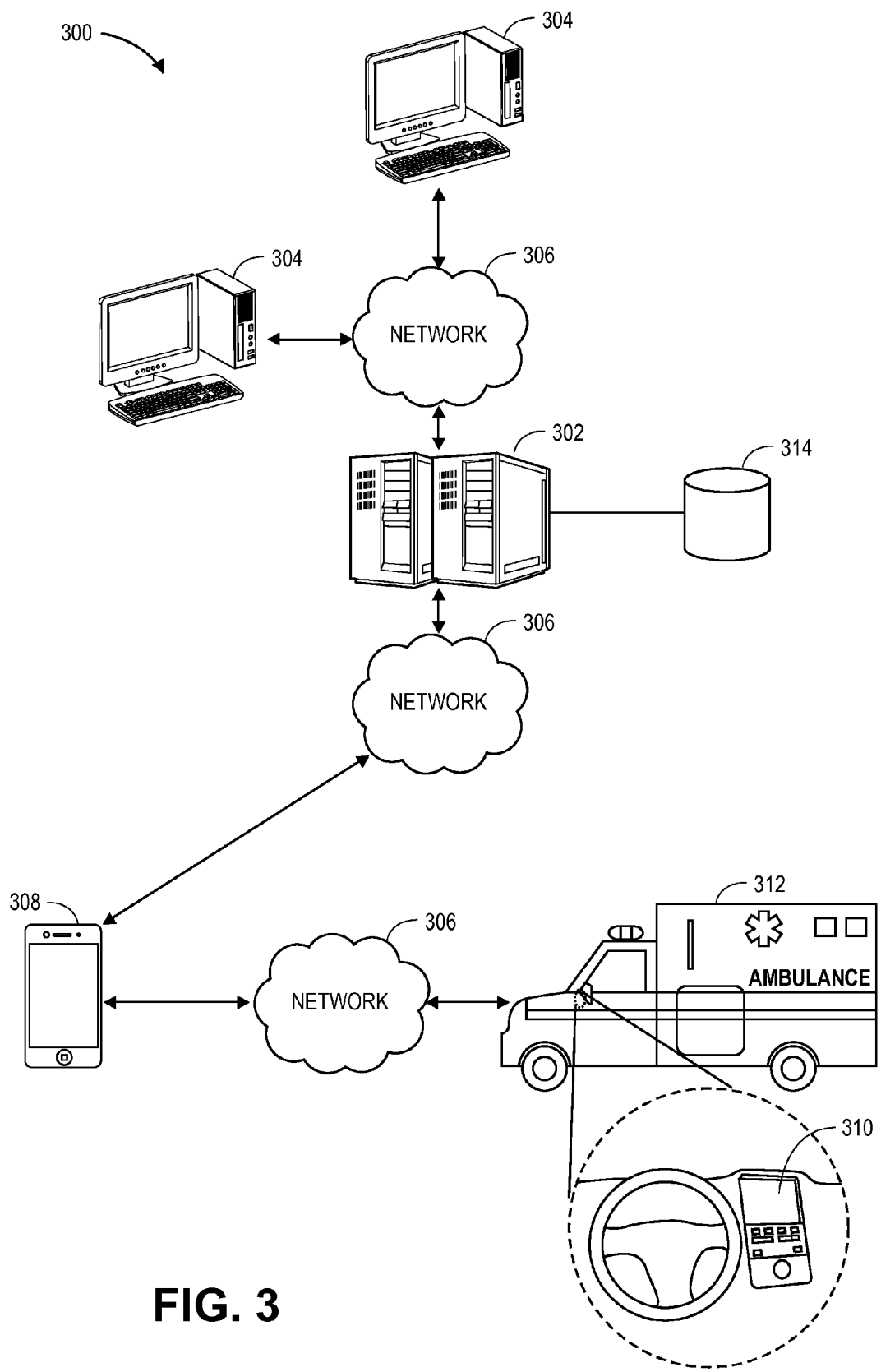
FIG. 3 is a schematic depiction of a system for remotely controlling functions of an emergency vehicle constructed in accordance with various embodiments of the present invention.

The computer program, system, and method of embodiments of the invention may be implemented in hardware, software, firmware, or combinations thereof using system 300, shown in FIG. 3, which broadly comprises server devices 302, computing devices 304, and a communications network 306. The server devices 302 may include computing devices that provide access to one or more general computing resources, such as Internet services, electronic mail services, and data transfer services, and the like.

The server devices 302 and computing devices 304 may include any device, component, or equipment with a processing element and associated memory elements. The processing element may implement operating systems, and may be capable of executing the computer program, which is also generally known as instructions, commands, software code, executables, applications, apps, and the like. The processing element may include processors, microprocessors, microcontrollers, field programmable gate arrays, and the like, or combinations thereof. The memory elements may be capable of storing or retaining the computer program and may also store data, typically binary data, including text, databases, graphics, audio, video, combinations thereof, and the like. The memory elements may also be known as a "computer-readable storage medium" and may include random access memory (RAM), read only memory (ROM), flash drive memory, floppy disks, hard disk drives, optical storage media such as compact discs (CDs or CDROMs), digital video disc (DVD), Blu-Ray™, and the like, or combinations thereof. In addition to these memory elements, the server devices 202 may further include file stores comprising a plurality of hard disk drives, network attached storage, or a separate storage network.

The computing devices 304 may specifically include mobile communication devices 308 (including wireless devices), work stations 304, desktop computers 304, laptop computers 304, palmtop computers 308, tablet computers 308, portable digital assistants (PDA) 308, smart phones 308, GPS units 310, vehicle computers 310 and vehicle computer systems 310, printers, and the like, or combinations thereof. In preferred embodiments, the mobile computing device 308 will have an electronic display, such as a cathode ray tube, liquid crystal display, plasma, or touch screen that is operable to display visual graphics, images, text, etc. In certain embodiments, the computer program of the invention facilitates interaction and communication through a graphical user interface (GUI) that is displayed via the electronic display. The GUI enables users (i.e., the consumer, emergency personnel, emergency vehicle operator, or an administrator) to interact with the electronic display by touching or pointing at display areas to provide information to the user control interface. In additional embodiments, the computing device 304 may include an optical device such as a digital camera, video camera, webcam, infrared scanner, optical scanner, or the like, such that the computing device can capture, store, and transmit digital images and/or videos. Any and all components may be directly in communication with a computing device, or wirelessly connected to a computing device through a communications network. Other embodiments may include an operably connected biometric security device, such as a fingerprint scanner or retina scanner, for preventative security access to the computing device.

The computing devices 304,308,310 may include a user control interface that enables one or more users to share information and commands with the computing devices 304,308,310 or server devices 302. The user interface may comprise one or more functionable inputs such as buttons, keyboard, switches, scrolls wheels, voice recognition elements such as a microphone, and pointing devices such as mice, touchpads, tracking balls, and styluses. The user control interface may also include a speaker for providing audible instructions and feedback. Further, the user control interface may comprise wired or wireless data transfer elements, such as a communication component, removable memory, data transceivers, and/or transmitters, to enable the user and/or other computing devices to remotely interface with the computing device 304,308,310.

The communications network 306 may be wired or wireless and may include servers, routers, switches, wireless receivers and transmitters, and the like, as well as electrically conductive cables or optical cables. The communications network 306 may also include local, metro, or wide area networks, as well as the Internet, or other cloud networks. Furthermore, the communications network 306 may include cellular or mobile phone networks, as well as landline phone networks, public switched telephone networks, fiber optic networks, or the like. The network may be the Internet, an intranet, or a telecommunications network. The server device may be any derivation of the computing device, operable to store and host data. The server device is operable to accept data packets from a computing device via a communications network, such as the Internet, a Wi-Fi link, Bluetooth, Near-Field Communications ("NFC"), a radio-frequency ("RF") link, or directly via a manual connection, such as a universal serial bus ("USB"), and Ethernet port.

Both the server devices 302 and the computing devices 304,308,310 may be connected to the communications network 306. Server devices 302 may be able to communicate with other server devices 302 or computing devices 304, 308,310 through the communications network 306. Likewise, computing devices 304,308,310 may be able to communicate with other computing devices 304,308,310 or server devices 302 through the communications network 306. The connection to the communications network 306 may be wired or wireless. Thus, the server devices 302 and the computing devices 304,308,310 may include the appropriate components to establish a wired or a wireless connection. In some embodiments, the server device and the computing device may be the same computing device, wherein the computing device servers all functions of the server device.

The computer program of the invention may run on at least one computing device 304,308,310 or, alternatively, may run on one or more server devices 302. Thus, a first portion of the program, code, or instructions may execute on a first server device 302 or a first computing device 304, 308,310, while a second portion of the program, code, or instructions may execute on a second server device 302 or a second computing device 304,308,310. In some embodiments, other portions of the program, code, or instructions may execute on other server devices 302 as well. In additional embodiments of the invention, a portion of the information to implement the invention may be stored on the server device 302, while another portion may be stored on the one or more computing devices 304,308,310. The various processes described herein as being performed by or using the computer program may actually be performed by one or more computers, processors, or other computational devices, such as the computing devices 304,308,310 and/or server devices 302, independently or cooperatively executing portions of the computer program.

In certain embodiments of the invention, the computer program may be embodied in a stand-alone program downloaded on a computing device 304,308,310 or in a web-accessible program that is accessible by a user's computing device 304,308,310 via the network 306. For the stand-alone program, a downloadable version of the computer program may be stored, at least in part, on the server device 302. A user can download at least a portion of the computer program onto the computing device 304,308,310 via the network 306. In such embodiments of the invention, the computer program may be an "application," such as an "app" for a mobile device 308. After the computer program has been downloaded, the program can be installed on the computing device 304,308,310 in an executable format. The executable form of the program permits the user to access embodiments of the invention via an electronic resource, such as a mobile "app" or website. For the web-accessible computer program, the user may simply access the computer program via the network 306 (e.g., the Internet) with the computing device 304,308,310.

In one embodiment, segments of code of the computer program may be stored and executable on a computing device or central server within the system, so that an administrator may configure a particular emergency vehicle 312 and at least one vehicular function with at least one user ID and password. The computing device 304,308,310 or central server 302 is preferably connected to a network so that the information stored thereon may be accessible by user mobile computing devices, central control units on vehicles, and/or administrator workstations. Each emergency vehicle 312 can be associated with more than one user, and each user can be associated with more than one emergency vehicle 312. Configurations for users and emergency vehicles 312 may be stored on a central database 314 or "cloud" via a network, or may be stored on one or more computing devices 304,308,310 at least having network access to other components of the system. It is also within the scope of the invention to assume that security certificates associated to each user and each vehicle may be stored in a central location, such as the central database 314 or "cloud," for purposes of user authentication and account maintenance.

Figure 4:
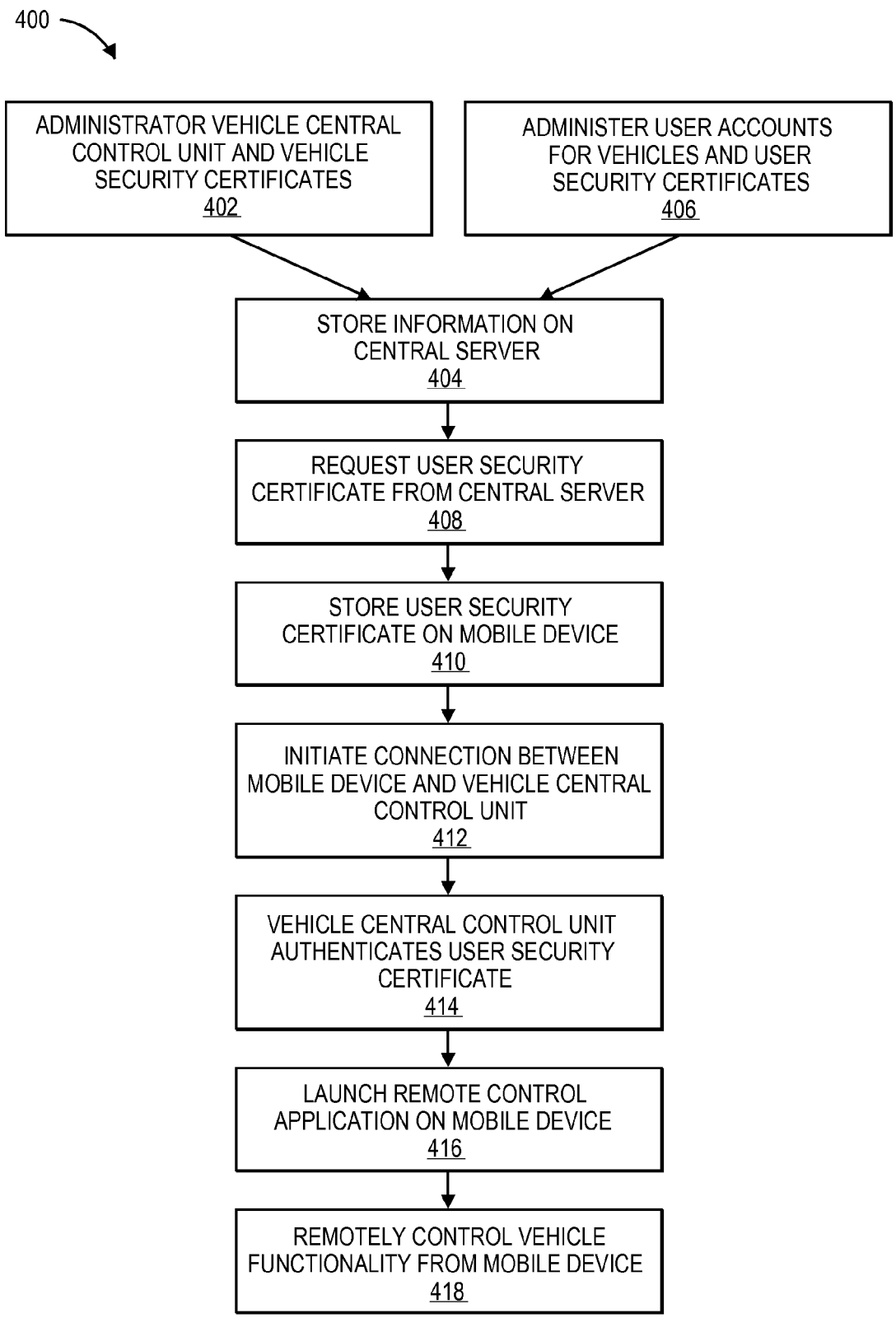
FIG. 4 is a flow chart depicting a more detailed exemplary process flow for embodiments of the invention.
Figure 5A:
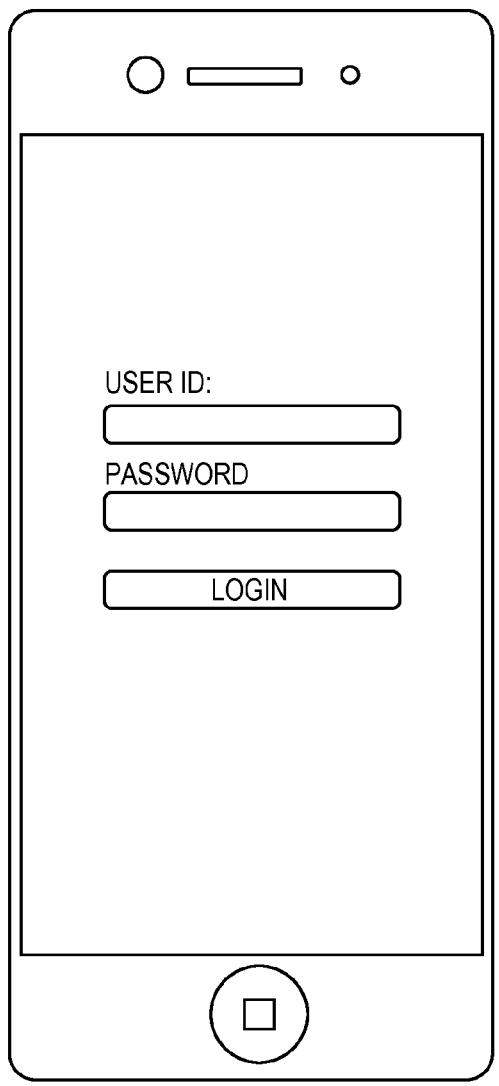
FIG. 5A is a first screen capture of the computer program of embodiments of the present invention and illustrating a login screen GUI.
Figure 5B:
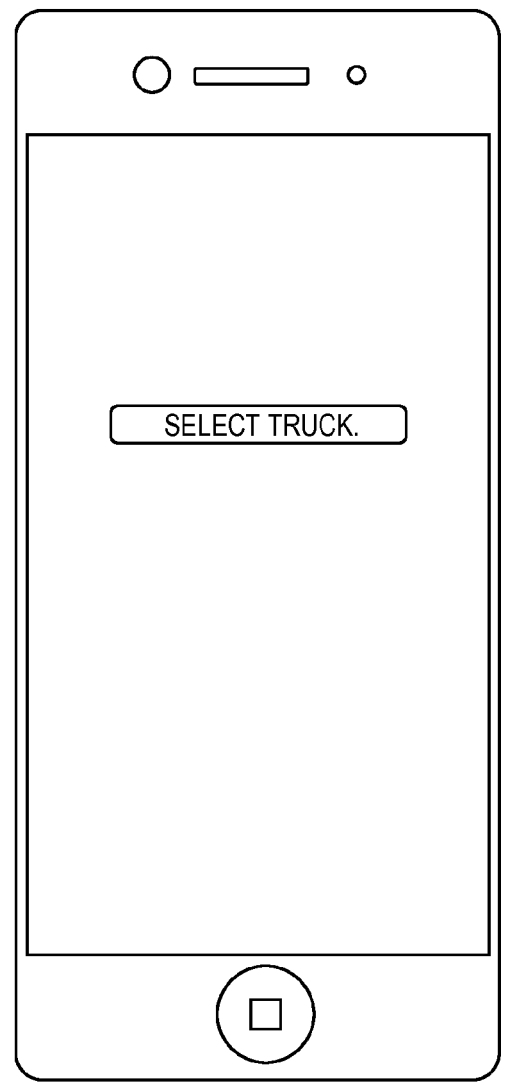
FIG. 5B is a second screen capture of the computer program of embodiments of the present invention and illustrating the first screen after a successful login, in particular, a first action GUI.
Figure 5C:
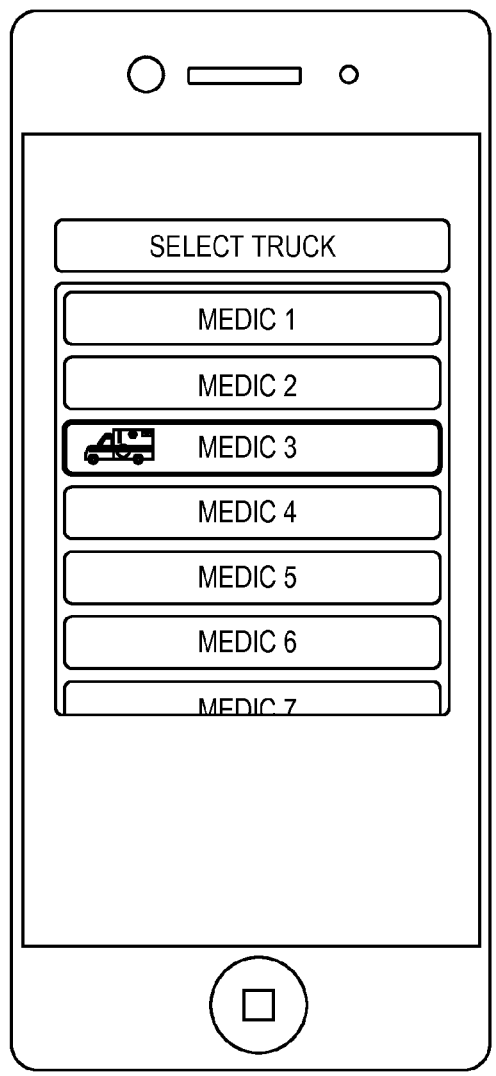
FIG. 5C is a third screen capture of the computer program of embodiments of the present invention and illustrating an emergency vehicle selection GUI.
Figure 5D:
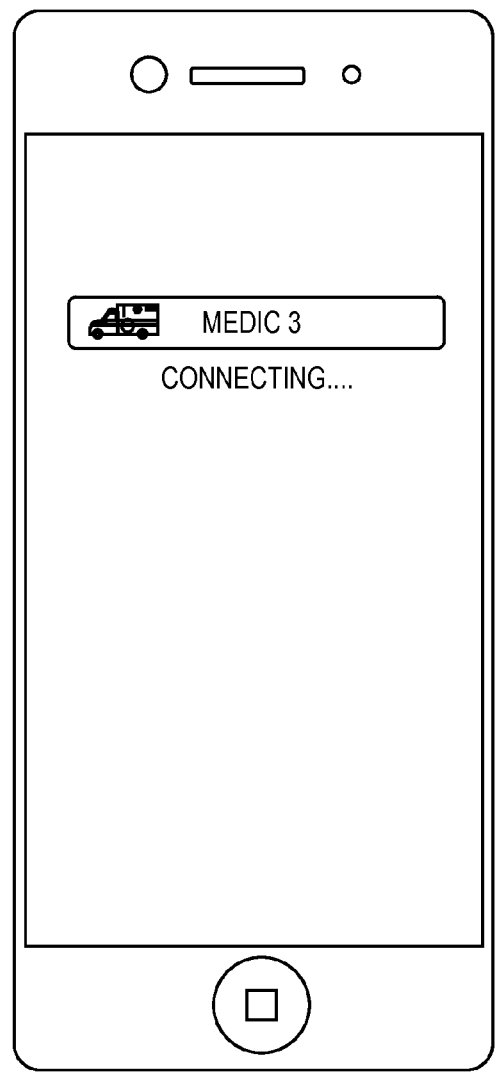
FIG. 5D is a fourth screen capture of the computer program of embodiments of the present invention and illustrating a connection status GUI.
Figure 6:
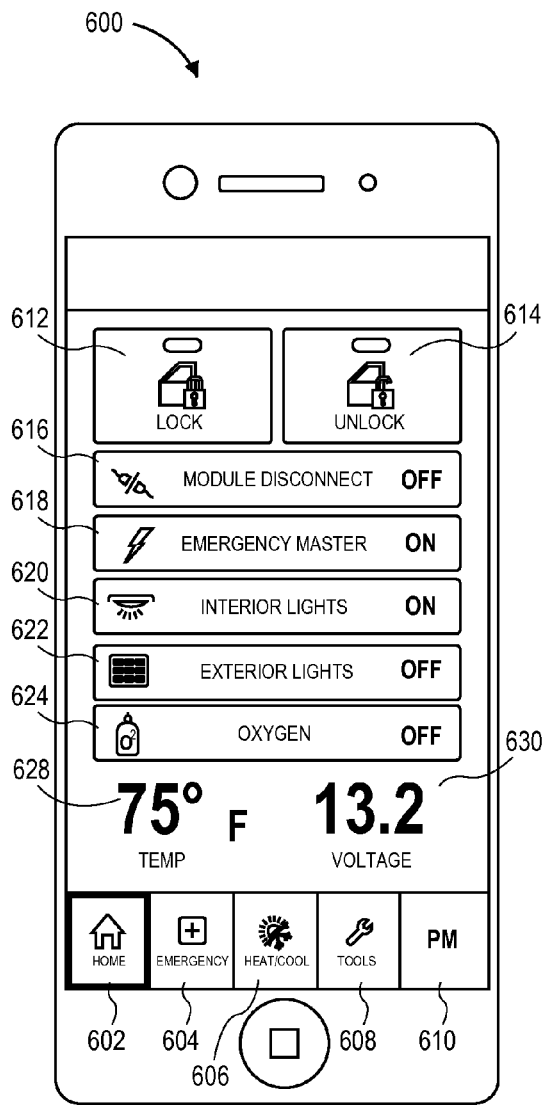
FIG. 6 is a screen capture of the computer program of embodiments of the present invention and illustrating a mobile computing device GUI and, in particular, an emergency vehicle control home screen.

FIG. 4 illustrates the process flow 400 of a preferred embodiment, where an administrator may configure each vehicle's central control unit 402 to store a predefined set of available functions and also store a unique vehicle security certificate. The administrator may store each vehicle's identifying information, security certificate information, and/or preset functions on a central server 404. Following the initial configuration of the vehicle central control unit, the same or second administrator may configure, via the central server, user access and permissions 406 and/or vehicle access and permissions. An administrator, provided the appropriate access, may have the ability to further limit or expand remote vehicle functions for each user to each vehicle based on desired access permissions. All changes made to the configuration data of the system may be stored on the central server database accessible via network connection. The central server database may be operable to store any or all details related to each user, details related to each vehicle, user security certificates, vehicle security certificates, and/or user-to-vehicle relationships (i.e., access permissions).

In one embodiment, a user, via a network accessible application on a mobile computing device, may access the central server via a network and request 408 general access to a particular or predetermined vehicle's central control unit. After the user communicates the appropriate credentials necessary for access, the central server may deliver 410 a user security certificate to the mobile computing device for use in communication with the particular vehicle's central control unit. Other embodiments may allow the transfer of security certificates via hard-wired communication directly to the server or the vehicle's central control unit. Even further embodiments may allow for the portability of security certificates via a removable memory card. Security certificates may also be downloaded and stored 410 onto a computing device from a central server via a web-based application. Upon the receipt and storage of a user security certificate on the mobile computing device, a user may attempt secure communications 412 with the vehicle central control unit. In a preferred embodiment, communications between the mobile computing device and the vehicle central control unit are wireless and encrypted through a communications network as described herein. In preferred embodiments, the vehicle central control unit is operably connected to a communications module, the communications module being a device enabling wireless connectivity to the communications network and operable to connect to at least one mobile computing device. In another embodiment, the communications module may be a device operably connected to the vehicle central control unit, the communications module configured to create a wireless communications network for accepting wireless communications from at least one mobile computing device.

In one embodiment, a mobile computing device will connect to a vehicle central control unit via the communications network. The communications network may be unencrypted and open, or may be secured using any known network encryption protocol or standard (i.e., WPA, WEP, WPA2, WPA2-PSK, WPA2-ENT, etc.) Once the initial connection is accomplished, a negotiation may take place, in which the mobile computing device presents the stored user security certificate to the vehicle central control unit, and the vehicle central control unit verifies or denies the validity of the user security certificate 414. If a user security certificate is denied by the vehicle, the vehicle central control unit may block further connection attempts from the mobile computing device, or may allow for further certification attempts up to a predefined limit. If a user security certificate is approved, the mobile computing device may be operably connected to the vehicle central control unit for remote control of the functions configured for the particular user to the particular vehicle.

In one embodiment, once a mobile computing device and a vehicle central control unit have been connected 412 via the communications network and security certificates have been validated 414, the mobile computing device user may execute a computer program 416 presenting a GUI for remotely controlling 418 various functions of the vehicle. Embodiments of the GUI after a successful network connection may present the user with an initial vehicle login screen and vehicle selection screen. See FIGS. 5A-D. Embodiments of the GUI control screens, See FIGS. 7-10, may include, but are not limited to, the following functions: lock/unlock doors, turn dome lights timer on/off, turn fluorescent lights timer on/off, read inside temperature, check battery voltage, download system information, run system diagnostics, remote start the vehicle, start heat/cool system, adjust temperature, prepare oxygen tank, contact the dealer, contact the service department, control cab windows, determine vehicle GPS location, receive maintenance reminders, read tire pressure, etc.

Figure 7:
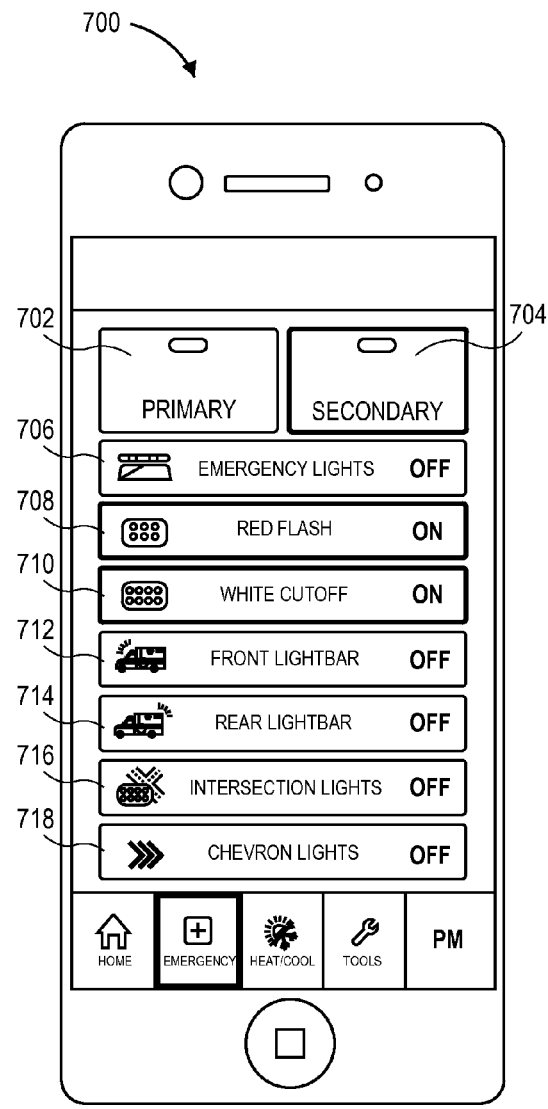
FIG. 7 is a screen capture of the computer program of embodiments of the present invention and illustrating a mobile computing device GUI and, in particular, an emergency vehicle Emergency function control screen.
Figures 8A, 8B:
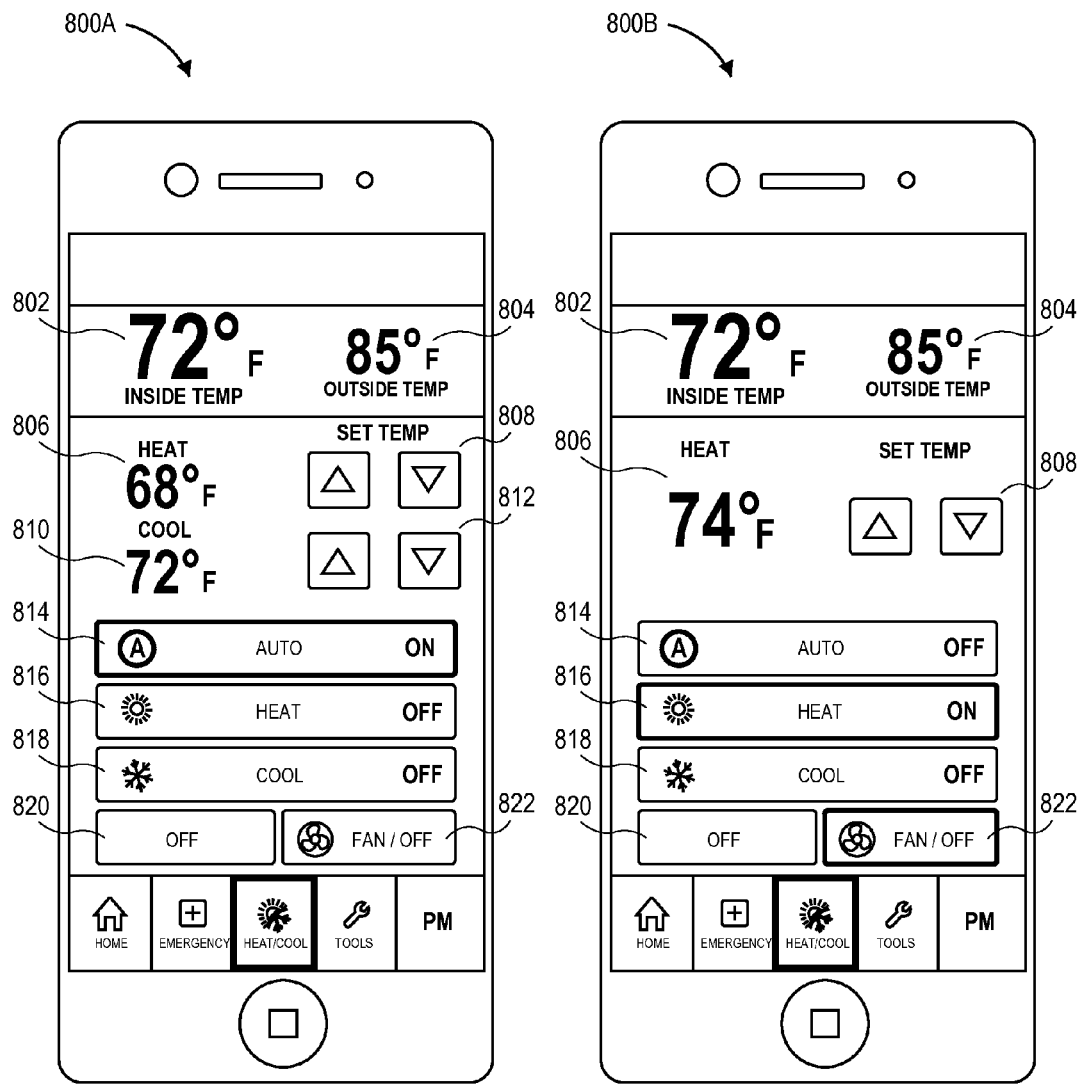
FIG. 8A is a first screen capture of the computer program of embodiments of the present invention and illustrating a mobile computing device GUI and, in particular, an emergency vehicle Heat/Cool function control screen for configuring auto temperature settings.
FIG. 8B is a second screen capture of the computer program of embodiments of the present invention and illustrating a mobile computing device GUI and, in particular, an emergency vehicle Heat/Cool function control screen for setting the heat thermostat.
Figure 9A:
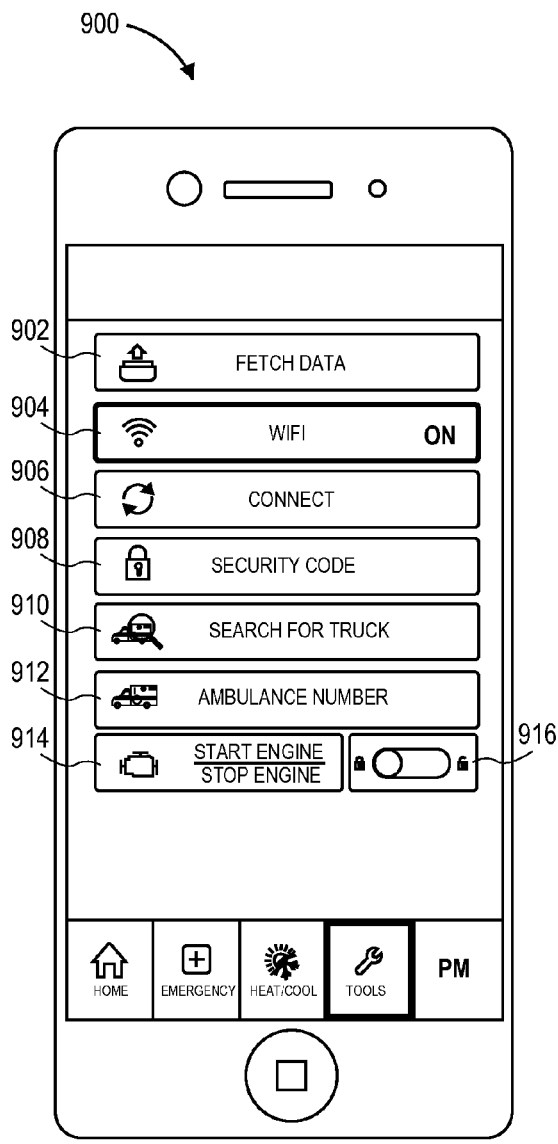
FIG. 9A is a first screen capture of the computer program of embodiments of the present invention and illustrating a mobile computing device GUI and, in particular, an emergency vehicle Tools control screen.
Figure 9B:
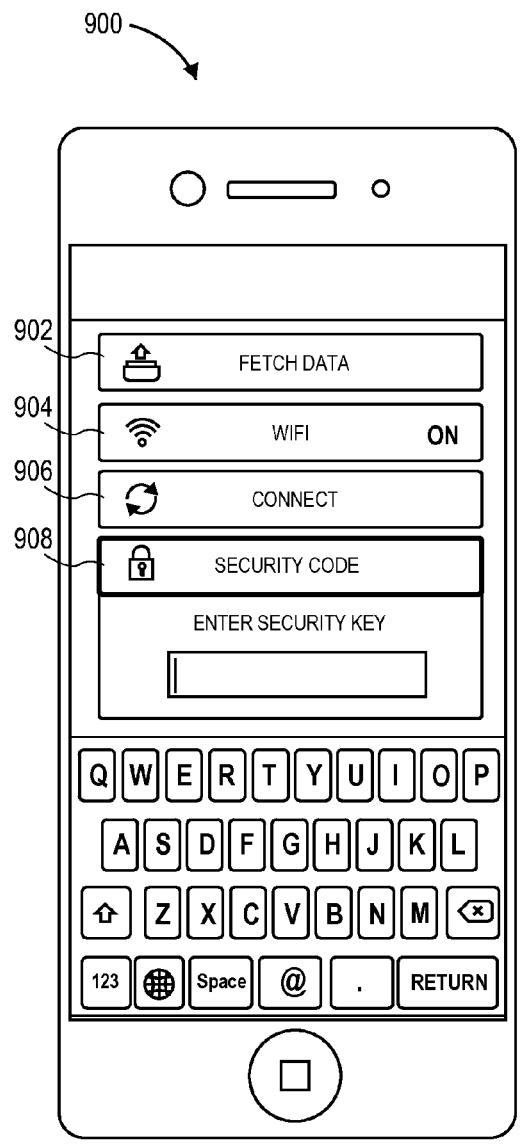
FIG. 9B is a second screen capture of the computer program of embodiments of the present invention and illustrating a mobile computing device GUI and, in particular, an emergency vehicle Tools control screen for entering a WiFi security key.
Figure 10A:
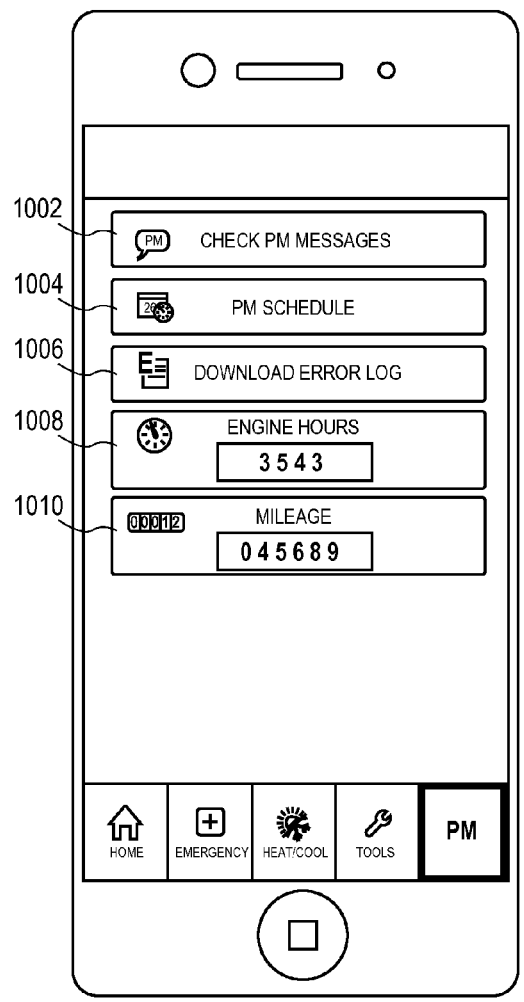
FIG. 10A is a first screen capture of the computer program of embodiments of the present invention and illustrating a mobile computing device GUI and, in particular, an emergency vehicle Preventative Maintenance ("PM") control screen.
Figure 10B:
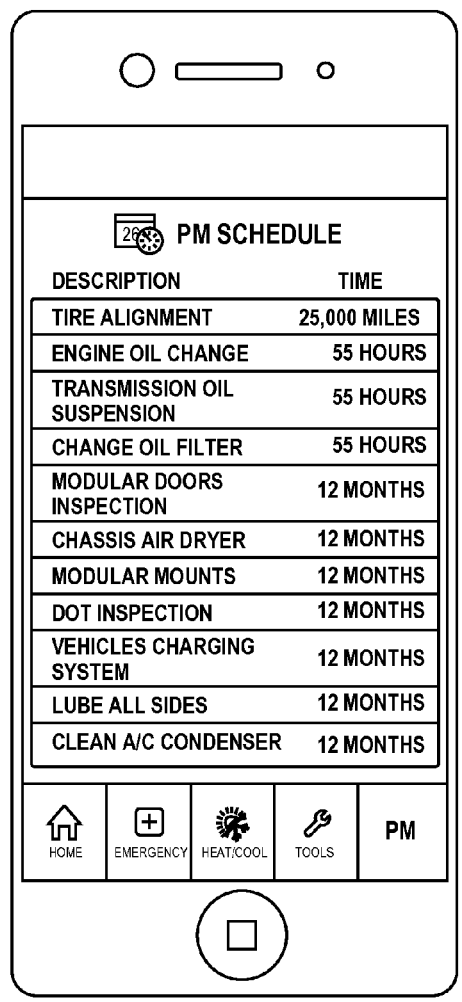
FIG. 10B is a second screen capture of the computer program of embodiments of the present invention and illustrating a mobile computing device GUI and, in particular, an emergency vehicle Preventative Maintenance ("PM") control screen displaying a vehicle's maintenance schedule.
Figure 10C:
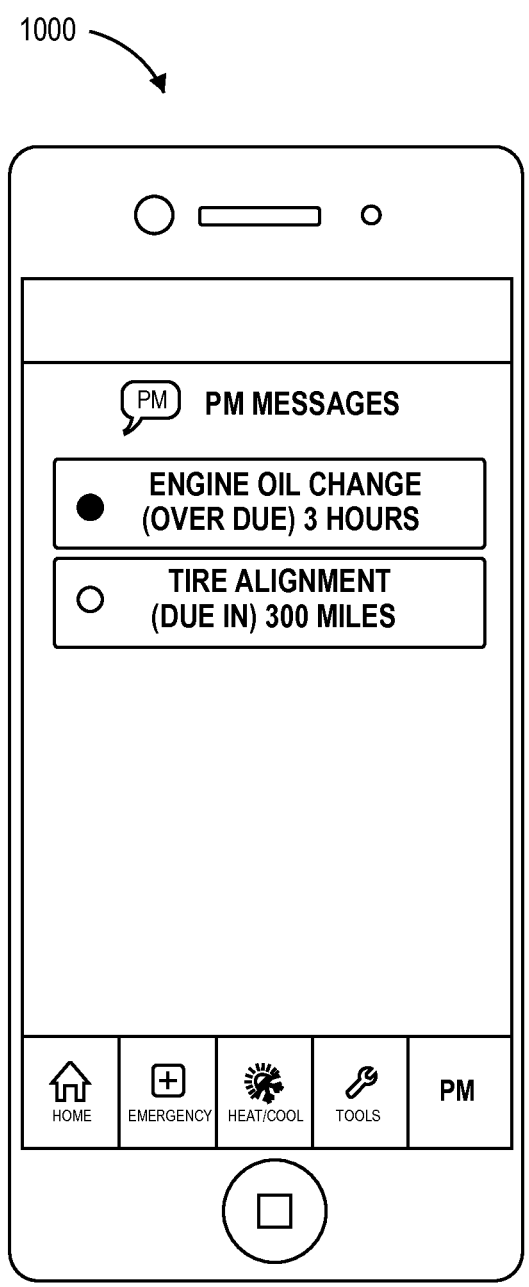
FIG. 10C is a third screen capture of the computer program of embodiments of the present invention and illustrating a mobile computing device GUI and, in particular, an emergency vehicle Preventative Maintenance ("PM") control screen for displaying automated messages received from the vehicle central control unit.

In a preferred embodiment, the GUI may be divided into different screens with different functions, i.e., Home, Emergency, Heat/Cool, Tools, and Preventative Maintenance ("PM"). See FIGS. 7-10. The Home screen, among all other screens, may present shortcuts to each screen such as Home 602, Emergency 604, Heat/Cool 606, Tools 608, and Preventative Maintenance 610. A Home screen 600 may display a configuration of virtual switches related to: lock doors 612, unlock doors 614, connect/disconnect from central control unit 616, turn on/off emergency master lights 618, turn off/on interior lights 620, turn off/on exterior lights 622, turn off/on oxygen tank 624, read inside temperature 628, read battery voltage 630. FIG. 7 illustrates an Emergency screen 700 that may display a configuration of virtual switches related to: primary controls 702, secondary controls 704, enable/disable emergency lights 706, enable/disable red flash 708, enable/disable white cutoff 710, enable/disable front light bar 712, enable/disable rear light bar 714, enable/disable intersection lights 716, enable/disable chevron lights 718. FIG. 8A-D illustrates a Heat/Cool screen 800 that may display a configuration of virtual displays and/or switches related to: read inside temperature 802, read outside temperature 804, display/set heat thermostat 806,808, display/set cool thermostat 810,812, automatically set vehicle temperature 814, turn on/off heater 816, turn on/off air conditioning 818, turn on/off climate control 820, turn on/off internal fan 822. FIG. 9A-B illustrate a Tools screen 900 that may display a configuration of virtual switches related to: fetch data 902, enable/disable Wi-Fi 904, connect to central control unit 906, enter security key 908, search for vehicle 910, set/read vehicle number 912, start/stop engine 914, lock/unlock cabin doors 916. FIGS. 10A-C illustrate a Preventative Maintenance screen 1000 that may display a configuration of virtual displays and/or switches related to: check Preventative Maintenance messages 1002, Preventative Maintenance schedule 1004, download error log 1006, read engine hours 1008, read vehicle mileage 1010. The arrangement of all screens and functionalities as described herein are merely exemplary and are not intended to be limiting. Screens, displays, views, and toggle configurations may be configured having any combination or arrangement of the above listed features and functionalities. It is within the scope of this invention that any vehicle function or diagnostic that may be operably connected to the electrical system and thus controllable by or in communication with the central control unit may be configured to be remotely controlled and/or displayed by the computer program of embodiments of this invention.

In one embodiment of the invention, each function of the vehicle that is controllable by the central control unit is operably controlled by at least one module, with the at least one module operable to receive a control signal from the central control unit. Upon the receipt of a command from an operably connected mobile computing device, the central control unit may generate a control signal and send the control signal to a particular module configured to carry out the particular function. For example, a vehicle ignition module may be configured to remotely start the vehicle upon the central control unit's receipt of a command to start the engine. Each module may perform one or more functions of the vehicle as intended. Modules may also be designed to be aware of states of each particular function performed. For example, a vehicle ignition module may be configured to start the engine when a command to remotely start the vehicle is sent to the central control module. The vehicle ignition module may be operable to detect the state (on/off) of the engine, and relay the status of the engine back to the central control module for reporting back to the mobile computing device. A door lock module may be operable to detect the state (locked/unlocked) of the doors and relay the status of the door locks back to the central control module for reporting back to the mobile computing device. In another embodiment, the GUI of the mobile computing device may report to the user that the particular function has successfully been performed or is currently being performed by the central control unit and any operably connected modules associated with the particular function.

In one embodiment, the mobile computing device may be a mobile computing device with cellular data connectivity. The ability for a mobile computing device to sync with a server via a cellular data connection may facilitate synchronization of data and other notifications received from a vehicle's central control unit to the user's mobile computing device, and further store the data to a central database or "cloud." It is within the scope of this invention to assume that data on one or more vehicles can be viewed by an administrator for updates on vehicle statuses and maintenance reminders. In another embodiment, connectivity to a central server via a cellular data connection may allow for an administrator to perform administrative tasks to a vehicle through a verified user's mobile computing device, such as read vehicle information, update vehicle information, execute available functions on the vehicle, or determine vehicle location.

Although the invention has been described with reference to the preferred embodiment(s), it is noted that equivalents may be employed and substitutions made herein without departing from the scope of the invention. Thus, the invention described herein is entitled to those equivalents and substitutions that perform substantially the same function in substantially the same way.

Having thus described various embodiments of the invention, what is claimed as new and desired to be protected by Letters Patent includes the following:

1. A method of remotely controlling an emergency vehicle electrical system, said method comprising:
   storing on a central server (i) a predefined set of functions for the emergency vehicle available to be remotely controlled, (ii) a unique vehicle security certificate for the emergency vehicle, and (iii) a user security certificate;
   transmitting from the central server to the emergency vehicle (i) the predefined set of functions available to be remotely controlled, and (ii) the unique vehicle security certificate for the emergency vehicle;
   configuring a central control unit of the emergency vehicle to store (i) the predefined set of functions available to be remotely controlled, and (ii) the unique vehicle security certificate;
   accessing, via a mobile computing device of a user, the central server to request access to the central control unit of the emergency vehicle by the user's mobile computing device;
   transmitting from the central server to the user's mobile computing device the user security certificate;
   installing the user security certificate on a mobile computing device of a user, the user security certificate configured to enable secure communications to the central control unit, the unique vehicle security certificate configured to enable said secure communications;
   configuring the central control unit of the emergency vehicle with user permissions, to thereby limit the functions available to be remotely controlled by the user to a subset of the predefined set of functions;
   selecting, via the mobile computing device, a virtual switch representing the emergency vehicle from a set of two or more virtual switches representing emergency vehicles presented on a display of the mobile computing device;
   connecting the mobile computing device to the central control unit of the emergency vehicle through a wireless network, said central control unit operable to perform the predefined set of functions of the emergency vehicle, wherein at least one function is activate emergency lights;
   selecting, via the mobile computing device, a virtual shortcut from a plurality of virtual shortcuts presented on the display of the mobile computing device, wherein each of the virtual shortcuts is associated with a control screen corresponding to a group of functions included within the predefined set of functions of the emergency vehicle;
   inputting a command on the mobile computing device, wherein the command corresponds to one or more functions of the emergency vehicle;
   transmitting the command to the central control unit through the network; and
   performing the one or more functions of the emergency vehicle.

2. The method of claim 1, wherein the performing the one or more functions step further comprises generating a control signal according to the command, and transmitting said control signal to a corresponding module configured to perform the one or more functions.

3. The method of claim 2, wherein the corresponding module is a module selected from the group consisting of a lights module, an emergency module, a keyless remote module, a temperature control module, a diagnostics module, and a maintenance module.

4. The method of claim 3, wherein the corresponding module comprises the lights module, wherein the lights module is configured to perform functions selected from the group consisting of activate dome lights, deactivate dome lights, activate fluorescent lights, deactivate fluorescent lights, activate loading lights, deactivate loading lights, activate scene lights, and deactivate scene lights.

5. The method of claim 3, wherein the corresponding module comprises the emergency module, wherein the emergency module is configured to perform functions selected from the group consisting of activate emergency lights, deactivate emergency lights, activate red flash, deactivate red flash, activate white cutoff, deactivate white cutoff, activate front lightbar, deactivate front lightbar, activate rear lightbar, deactivate rear lightbar, activate intersection lights, deactivate intersection lights, activate chevron lights, and deactivate chevron lights.

6. The method of claim 3, wherein the corresponding module comprises the keyless remote module, wherein the keyless remote module is configured to perform functions selected from the group consisting of start engine, kill engine, lock doors, unlock doors, open windows, and close windows.

7. The method of claim 3, wherein the corresponding module comprises the temperature control module, wherein the temperature control module is configured to perform functions selected from the group consisting of detect internal temperature, increase temperature, decrease temperature, and set thermostat.

8. The method of claim 3, wherein the corresponding module comprises the diagnostics module, wherein the diagnostics module is configured to perform functions selected from the group consisting of check battery voltage, view GPS location, view trip log, view mileage, view fuel level, and view fuel efficiency.

9. The method of claim 3, wherein the corresponding module comprises the maintenance module, wherein the maintenance module is configured to perform functions selected from the group consisting of remind to perform oil change, remind to perform tire rotation, remind to align tires, remind to adjust timing belt.

10. A non-transitory computer readable storage medium with an executable program stored thereon for controlling an emergency vehicle, said emergency vehicle having a central control unit with a unique vehicle security certificate stored thereon, said central control unit operably connected to an electrical system and further configured to perform one or more functions of the emergency vehicle, wherein the program instructs a processor to perform the following steps:
   access a central server to request access to the emergency vehicle, wherein the central server is configured to store user security certificates;
   receive, on a mobile computing device, a user security certificate from the central server, wherein the user security certificate and the unique vehicle security certificate are configured to enable secure communications between the mobile computing device and the central control unit;
   display, on a mobile computing device, a vehicle selection screen presenting a plurality of virtual switches indicative of a set of vehicles, with such set of vehicles including the emergency vehicle, wherein each of the emergency vehicles associated with the virtual switches is configured to have a plurality of functions remotely controlled by the mobile computing device;

receive, on the mobile computing device, a request from a user to establish a connection to the central control unit;

establish a wireless connection between the mobile computing device and the central control unit;

display, on the mobile computing device, a plurality of virtual shortcuts, wherein each of the virtual shortcuts is associated with a control screen corresponding to a set of functions included within the plurality of functions of the emergency vehicle;

display, on the mobile computing device, a set of functions of the emergency vehicle, wherein at least one function of said set is activate emergency lights;

receive, on the mobile computing device, a command from the user to perform one or more functions of the emergency vehicle; and transmit, from the mobile computing device, the command to the central control unit.

11. The executable program of claim 10, further instructing the processor to perform the step of: generate, on the central control unit, a control signal according to the command received from the mobile computing device, and transmitting said control signal to a corresponding module configured to perform the one or more functions.

12. The executable program of claim 11, wherein the corresponding module is a module selected from the group consisting of a lights module, an emergency module, a keyless remote module, a temperature control module, a diagnostics module, and a maintenance module.

13. The executable program of claim 12, wherein the corresponding module comprises the lights module, wherein the lights module is configured to perform functions selected from the group consisting of activate dome lights, deactivate dome lights, activate fluorescent lights, deactivate fluorescent lights, activate loading lights, deactivate loading lights, activate scene lights, and deactivate scene lights.

14. The executable program of claim 12, wherein the corresponding module comprises the emergency module, wherein the emergency module is configured to perform functions selected from the group consisting of activate emergency lights, deactivate emergency lights, activate red flash, deactivate red flash, activate white cutoff, deactivate white cutoff, activate front lightbar, deactivate front lightbar, activate rear lightbar, deactivate rear lightbar, activate intersection lights, deactivate intersection lights, activate chevron lights, and deactivate chevron lights.

15. The executable program of claim 12, wherein the corresponding module comprises the keyless remote module, wherein the keyless remote module is configured to perform functions selected from the group consisting of start engine, kill engine, lock doors, unlock doors, open windows, and close windows.

16. The executable program of claim 12, wherein the corresponding module comprises the temperature control module, wherein the temperature control module is configured to perform functions selected from the group consisting of detect internal temperature, increase temperature, decrease temperature, and set thermostat.

17. The executable program of claim 12, wherein the corresponding module comprises the diagnostics module, wherein the diagnostics module is configured to perform functions selected from the group consisting of check battery voltage, view GPS location, view trip log, view mileage, view fuel level, and view fuel efficiency.

18. The executable program of claim 12, wherein the corresponding module comprises the maintenance module, wherein the maintenance module is configured to perform functions selected from the group consisting of remind to perform oil change, remind to perform tire rotation, remind to align tires, remind to adjust timing belt.

19. An emergency vehicle control system comprising:
a communications component secured to an emergency vehicle, said communications component configured to wirelessly communicate with a mobile computing device;
a central control unit operably connected to the communications component, said central control unit comprising an executable program that enables the mobile computing device to control at least one function of at least one module in the emergency vehicle control system,
wherein said central control unit stores access permissions for two or more users, wherein control of the modules in the emergency vehicle is based on said access permissions,
wherein said central control unit stores a unique vehicle security certificate, wherein the unique vehicle security certificate, along with a user security certificate stored on the mobile computing device, is configured to enable secure communications between the mobile computing device and the central control unit;
a central server connected to a network, said central server at least remotely accessible by the mobile computing device for verifying user information and installing the user security certificate for secure communications between the mobile computing device and the central control unit;
an emergency module operably connected to the central control unit, said emergency module at least configured to activate emergency lights; and
a non-transitory computer readable storage medium with an executable program stored thereon, wherein the program instructs a processor on the mobile computing device to perform the following step—
display, on the mobile computing device, a vehicle selection screen presenting a plurality of virtual switches indicative of a set of vehicles, with such set of vehicles including the emergency vehicle, wherein each of the emergency vehicles associated with the information indicative of the set is configured to have one or more functions remotely controlled by the mobile computing device;
display, on the mobile computing device, a plurality of virtual shortcuts, wherein each of the virtual shortcuts is associated with a control screen corresponding to a set of functions included within the one or more functions of the emergency vehicle.

20. The emergency vehicle control system of claim 19, wherein the central server is further accessible by at least one workstation, said workstation operable to provide administrative access for vehicle administration.

21. The emergency vehicle control system of claim 19, wherein the central server is further accessible by at least one workstation, said workstation operable to provide administrative access for user account administration.

* * * * *